(12) United States Patent
Benz et al.

(10) Patent No.: US 7,203,271 B2
(45) Date of Patent: Apr. 10, 2007

(54) IONIZING RADIATION IMAGING SYSTEM AND METHOD WITH DECREASED RADIATION DOSE

(75) Inventors: Mark G. Benz, Lincoln, VT (US); Matthew W. Benz, Shrewsbury, MA (US)

(73) Assignee: Pediatric Imaging Technology, LLC, Lincoln, VT (US)

( * ) Notice: Subject to any disclaimer, the term of this patent is extended or adjusted under 35 U.S.C. 154(b) by 0 days.

(21) Appl. No.: 11/169,130

(22) Filed: Jun. 27, 2005

(65) Prior Publication Data

US 2005/0286678 A1 Dec. 29, 2005

Related U.S. Application Data

(60) Provisional application No. 60/583,382, filed on Jun. 28, 2004.

(51) Int. Cl.
*G01N 23/02* (2006.01)
(52) U.S. Cl. .......................... 378/19; 378/62; 378/98.8
(58) Field of Classification Search ................. 378/19, 378/62, 98.8
See application file for complete search history.

(56) References Cited

U.S. PATENT DOCUMENTS

| | | | | | |
|---|---|---|---|---|---|
| 4,887,285 | A | * | 12/1989 | Harding et al. | ............... 378/88 |
| 4,956,859 | A | * | 9/1990 | Lanza et al. | ................. 378/157 |
| 5,090,040 | A | * | 2/1992 | Lanza et al. | .................. 378/62 |
| 5,285,489 | A | * | 2/1994 | Ohtsuchi et al. | ............ 378/156 |
| 5,285,490 | A | * | 2/1994 | Bunch et al. | ................. 378/156 |
| 5,381,458 | A | * | 1/1995 | Deslattes | ................... 378/207 |
| 5,561,696 | A | * | 10/1996 | Adams et al. | ................. 378/58 |
| 5,596,620 | A | * | 1/1997 | Canistraro et al. | ............ 378/84 |
| 5,859,893 | A | * | 1/1999 | Moorman et al. | ........... 378/154 |
| 6,418,193 | B1 | * | 7/2002 | Albagli | ........................ 378/158 |
| 6,445,767 | B1 | * | 9/2002 | Karellas | ...................... 378/98.8 |
| 6,630,077 | B2 | * | 10/2003 | Shiang et al. | .......... 252/301.4 R |
| 6,965,661 | B2 | * | 11/2005 | Kojima et al. | .................. 378/4 |
| 6,973,158 | B2 | * | 12/2005 | Besson | ......................... 378/16 |
| 7,010,092 | B2 | * | 3/2006 | Winsor | ....................... 378/98.9 |
| 2004/0028181 | A1 | * | 2/2004 | Charles, Jr. et al. | ........... 378/92 |

OTHER PUBLICATIONS

Ron E. Cancer risks from medical radiation. *Health Phys.* 2003;85:47-59.
Brenner DJ, Elliston CD, Hall EJ, Berdon WE. Estimated risks of radiation-induced fatal cancer from pediatric CT. *AJR Am J Roentgenol.* 2001; 176:289-296.
Preston DL, Shimizu Y, Pierce DA, Suyama A, Mabuchi K. Studies of mortality of atomic bomb survivors: report 13, solid cancer and noncancer disease mortality:1950-1997. *Radiat Res.*2003;160:381-407.

(Continued)

*Primary Examiner*—Edward J. Glick
*Assistant Examiner*—Thomas R. Artman
(74) *Attorney, Agent, or Firm*—Downs Rachlin Martin PLLC

(57) ABSTRACT

A system and method for imaging a volume having a detector including a first atomic species with an absorption edge at a first wavelength. The system also includes a source having a second atomic species for emitting an ionizing energy. The second atomic species has a characteristic emission peak that substantially matches the absorption edge of the detector. A filter may be provided for blocking ionizing energy from the source in regions other than a region proximate the characteristic emission peak. Effective imaging with a lower radiation dose may be achieved with the system and method.

40 Claims, 3 Drawing Sheets

OTHER PUBLICATIONS

Hall EJ. Lessons we have learned from our children: cancer risks from diagnostic radiology. *Pediatr Radio.* 2002;32:700-706.

Fegal DW Jr. *FDA Public Health Notification: Reducing Radiation Risk from Computed Tomography for Pediatric and Small Adult Patients.* Rockville, MD: Food and Drug Administration; 2001. Available at: http://www.fda.gov/cdrh/safety/110201-ct.html Accessed May 9, 2004.

Soceity for Pediatric Radiology and the National Cancer Institute. *Radiation and Pediatric Computed Tomography: A Guide for Health Care Providers.* Houston, TX: Society for Pediatric Radiology and the National Cancer Institute; 2002. Available at: http://www.cancer.gov/cancerinfo/causes/radation-risks-pediatric-CT. Accessed May 9, 2004.

Linton OW, Mettler FA Jr. National conference on dose reduction in CT, with an emphasis on pediatric patients. *AJR Am J Roentgenol.* 2003; 181:321-329.

Slovis TL. The ALARA concept in pediatric CT: myth or reality? *Radiology.* 2002;223:5-6.

Brody AS, Guillerman RP. Radiation risk from diagnostic imaging. Pediatr Ann. 2002;31:643-647.

Slovis TL, ed. The ALARA concept in pediatric CT intelligent dose reduction: multidisciplinary conference organized by the Society of Pediatric Radiology. *Pediatr Radiol.* 2002;32:217-313.

Slovis TL. Children, computed tomography radiation dose, and the as low as reasonably achievable (ALARA) concept. *Pediatrics.* 2003;112:971-972.

Morris WG. *Tungsten Spectra Collected Using Rdige Microfocus System and GE X-Ray Detector: Microanalysis Data Base.* Schenectady, NY: General Electric Global Research Center, 2002. Personal Communication.

Cullity BD. *Elements of X-Ray Diffraction.* Reading, MA: Addison-Wesley;1956:9-17.

Brandes EA, Brook GB. *Smithell's Metal Reference Book.* 7th ed. Oxford, UK: Butterworth-Heinmann;1992:4-6.

Suleiman OH, Spelic DC, McCrohan JL, Symonds GR, Houn F. Mammography in the 1990s: the United States and Canada. *Radiology.* 1999; 210:345-351.

Food and Drug Administration. *Nationwide Evaluation of X-Ray Trends: Twenty-Five years of NEXT.* Rockville, MD: Food and Drug Administration;2003. Available at: www.crcpd.org/publications. asp#NEXT Accessed May 9, 2004.

Monsees BS. The Mammography Quality Standards Act: an overview of the regulations and guidance. *Radiol Clin North Am.* 2000;38:759-772.

Democratic Staff of the Committee on Energy and Commerce. HR4888:Mammography Quality Standards Reauthorization Act of 2002. Available at: http://house.gov/commerce_democrats/mqsa/summary.shtml.

Frush DP, Donnelly LF, Rosen NS. Computed tomography and radiation risks;what pediatric health care providers should know. *Pediatrics.*2003;112:951-957.

American Academy of Pediatrics, Committee on Quality Improvement, Commission on Clinical Policies and Research, American Academy of Family Physicians. The management of minor closed head injury in children. *Pediatrics.* 1999;104:1407-1415.

\* cited by examiner

IONIZING RADIATION IMAGING SYSTEM AND METHOD WITH DECREASED RADIATION DOSE

RELATED APPLICATION DATA

This application claims the benefit of priority of U.S. Provisional Patent Application Ser. No. 60/583,382, filed Jun. 28, 2004, and titled "Enhanced X-Ray-Detector-Based System and Method for CT", which is incorporated by reference herein in its entirety.

FIELD OF THE INVENTION

The present invention generally relates to the field of imaging using ionizing radiation. In particular, the present invention is directed to an ionizing radiation imaging system and method with decreased radiation dose.

BACKGROUND OF THE INVENTION

Ionizing radiation, such as x-ray and gamma radiation, has been used for years in imaging systems, particularly in medical imaging. Exposure to ionizing radiation has many documented harmful effects, one of the most serious of which is the induction of fatal cancers. All human suspects are susceptible to ionizing radiation in the doses provided by typical imaging technology. However, children are reported to be at approximately ten times greater risk than an average middle-aged adult. This increased susceptibility to the negative effects of ionizing radiation is due in part to the developing and dividing cells of a child's body, which are more susceptible to radiation-induced neoplastic transformation than the cells of an adult. Additionally, children have a greater lifespan remaining than a middle-aged adult for the genotoxic effects of the radiation to manifest.

X-ray radiation, such as that used in a conventional chest x-ray, has been used constructively for a long time to produce medical images. Another type of ionizing radiation imaging technology more recently used is computer tomography ("CT"), typically using x-ray radiation as a source. Conventional x-ray CT technology measures the differential absorption of x-rays passing through the body of an object (or volume) and uses computer analysis of the data by tomographic techniques to produce an image. Conventional x-ray CT technology doses have been found to be similar to the doses that were received by World War II Japanese atomic bomb survivors, a group in whom excess cancer mortality has been observed. Using data from such survivors, Brenner et al. has predicted that the use of conventional x-ray CT technology on infants and children may cause the eventual cancer-related death of 1 out of every 1000 children examined using such CT technology. See Brenner et al., "Estimated risks of radiation-induced fatal cancer from pediatric CT," AJR Am J Roentgenol. 2001; 176:289–296. This rate is considered by many to be unacceptably high. As an example, of the approximately 12 million infants and children that have been imaged by CT in the United States since the observations by Brenner et al. in 2001, approximately 12,000 are expected to die later in life from cancer initiated by the CT procedure.

Imaging systems that employ ionizing radiation typically include a source for providing the ionizing radiation to an object and a detector for detecting the ionizing radiation that passes through the object. In some cases film serves as the detector. In other cases electronic detectors connected to computer imaging devices are utilized. Adjustments to a source (milliamp, mA and/or kilovolt, kV) can be made to assist in obtaining a desired image exposure. Turning up the total power of the source (and thus the dose of radiation received by the object) can produce a higher resolution image. Turning down the total power of the source (lowering the radiation dose) can produce lower quality images.

Attempts have been made to employ reduced and more judicious use of ionizing radiation imaging with objects prone to increased effect from the radiation doses. Despite this approach with children and infants, the total number of pediatric diagnostic CT images continues to grow each year. Another method used to decrease exposure to ionizing radiation involves adjusting exposure parameters on existing instrumentation to deliver an "as low as reasonably achievable" (ALARA) radiation dose. Exposure parameters include tube current (mA), peak kilovolatage (kVp), pitch, slice thickness, and table speed. Adjustment of exposure parameters is limited by the existing technology (for example, sources and detectors) and can only decrease the total radiation dose to certain levels while still achieving desirable image quality. Further, despite attempts to reduce radiation dose, a wide variability in image scanning techniques still exists that expose many objects to higher than necessary radiation doses. In addition, multi-detector (multi-slice) image scanners are now being used and are inherently more complex, presenting an additional challenge with respect to dose reduction. Systems and methods for further reduction of radiation dose to imaging objects is desired.

SUMMARY OF THE INVENTION

In one embodiment, the present invention provides a system for imaging a volume. The system includes a detector having a first atomic species with a predetermined absorption edge having a first wavelength. The system also includes a source having a second atomic species, the second atomic species for emitting an ionizing energy including wavelengths at or near the absorption edge, the second atomic species having a characteristic emission peak at a second wavelength that substantially matches the first wavelength.

In another embodiment, the present invention provides a method of producing a system for imaging a volume. The method includes (a) providing a detector atomic species having an absorption edge with a corresponding first wavelength; (b) providing a source atomic species having a characteristic emission peak that has a second wavelength that substantially matches the first wavelength; (c) including the source atomic species in a source element, the source element for delivering an ionizing radiation to the volume; and (d) including the detector atomic species in a detector element, the detector element configured to detect the ionizing radiation that passes through the volume.

In yet another embodiment, the present invention provides a method of imaging a volume. The method includes (a) providing a detector having a first atomic species with an absorption edge; (b) providing a source having a second atomic species with a characteristic emission peak that substantially matches the absorption edge; (c) delivering an ionizing radiation from the source to the volume; (d) using the detector to detect the ionizing radiation that passes through the volume; and (e) producing an image based on the ionizing radiation detected by the detector.

In still another embodiment, the present invention provides an imaging system for obtaining an image of a volume.

The system includes a source operatively configured to provide an ionizing energy, the source including a first atomic species for producing the ionizing energy. The system also includes a detector having a second atomic species capable of absorbing the ionizing energy, the second atomic species having an absorption edge. The source provides the ionizing energy to the volume at wavelengths limited to a narrow imaging band, the narrow imaging band including a wavelength at or below the absorption edge and including only wavelengths necessary to achieve a predetermined desired quality of the image.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION

The present invention provides an ionizing radiation imaging system and method that reduces the radiation dose imparted on a object being imaged, while attaining a high quality image. By matching a peak emission of a source to a peak absorbance of a detector, high quality images can be attained using a minimized radiation dose to a object to be imaged.

Figure 1:
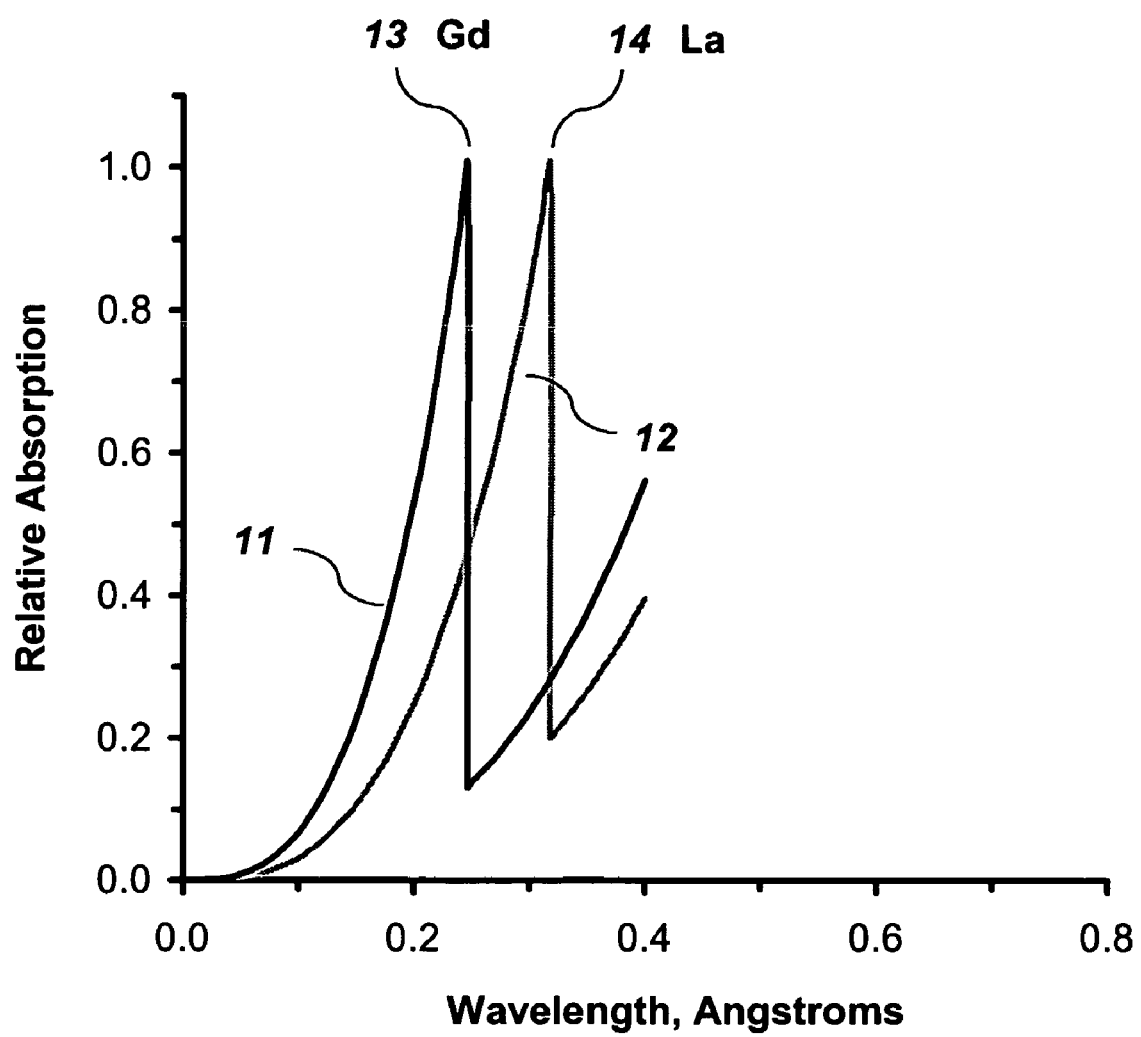
FIG. 1 shows a plot of the relative x-ray absorption vs. wavelength for gadolinium and lanthanum.

FIG. 1 illustrates a plot 11 of relative energy absorption versus energy wavelength for gadolinium and a plot 12 of relative energy absorption versus energy wavelength for lanthanum. Gadolinium and lanthanum are examples of atomic species that can be included in a detector according to the present invention. Plot 11 shows an absorption edge 13, or absorption maximum, for gadolinium at energy of wavelength of about 0.25 Angstroms (A). Plot 12 shows an absorption edge 14 for lanthanum at about 0.32 A. As can be seen in plots 11 and 12, maximum absorption of energy by an atomic species occurs at a wavelength that is at or just below its absorption edge. Energy at a wavelength just above an absorption edge is absorbed to a relatively much lower degree.

Figure 2:
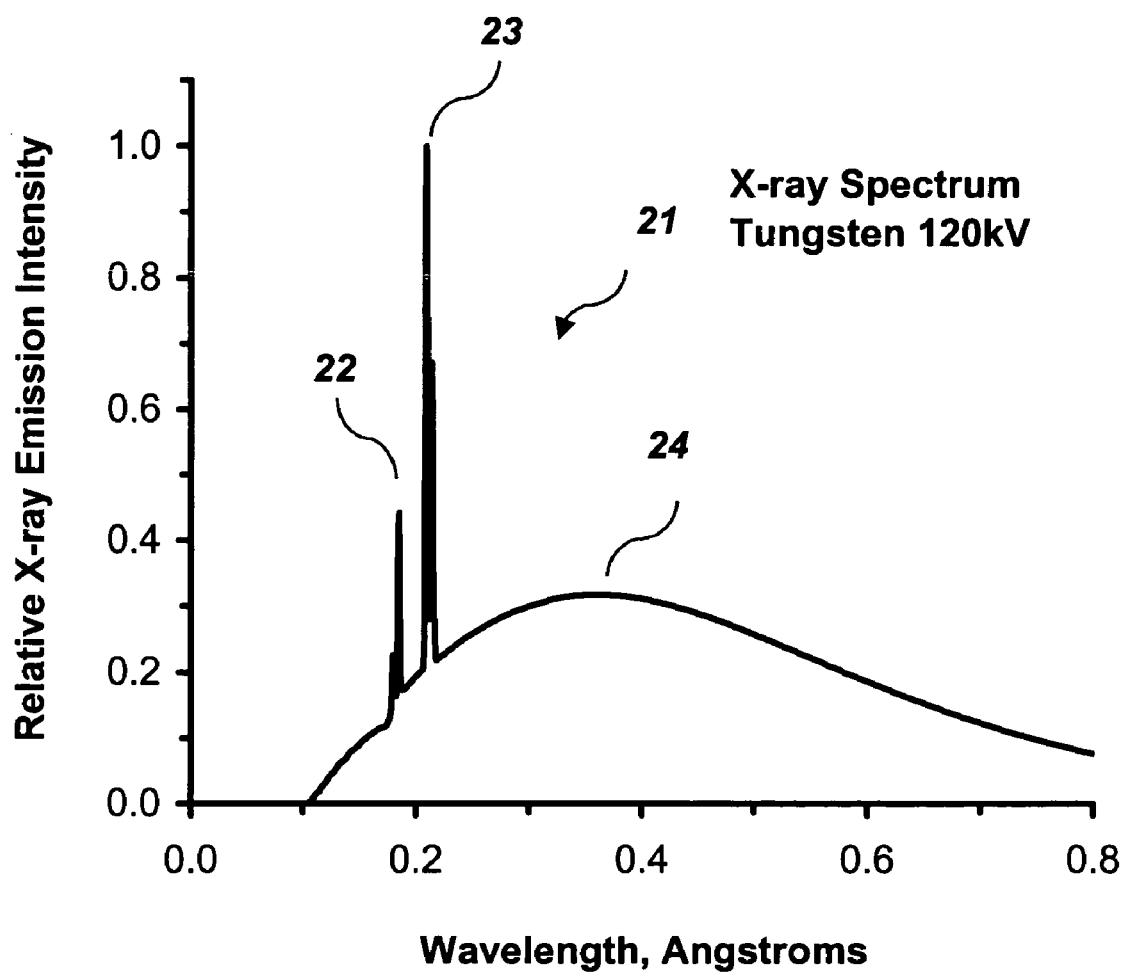
FIG. 2 shows a plot of the relative x-ray emission intensity vs. wavelength for tungsten excited by 120 kV electrons.

FIG. 2 illustrates a plot 21 of relative energy emission intensity for tungsten in the x-ray range. Tungsten is an example of an atomic species that can be included in a source according to the present invention. Plot 21 includes a K-alpha-2 emission peak 22 and a K-alpha-1 emission peak 23. Emission peaks 22 and 23 are specific to individual atomic species and are referred to as characteristic peaks. Differing atomic species will produce ionizing radiation with different characteristic peaks. Plot 21 also includes a "white radiation" peak 24 that covers a broad band of wavelengths. Changing a deceleration voltage of a source can change a "white radiation" peak.

Conventional ionizing radiation imaging detectors are designed to work at wavelengths far from an absorption edge, such as absorption edge 13. Typical imaging sources produce ionizing radiation across a broad spectrum of wavelengths. Conventional imaging detectors must respond similarly to energy across this broad spectrum. In order to obtain linear results across the broad spectrum of the source, a conventional detector is tuned to operate at a flatter portion of its absorption curve than the absorption edge. The present invention takes advantage of an absorption edge of a detector atomic species by matching a strong emission peak of a source, such as K-alpha-1 emission peak 23 for tungsten, to the absorption edge of the detector. In doing so, sensitivity of the detector is maximized allowing lower levels of energy from a source to be used.

Figure 3:
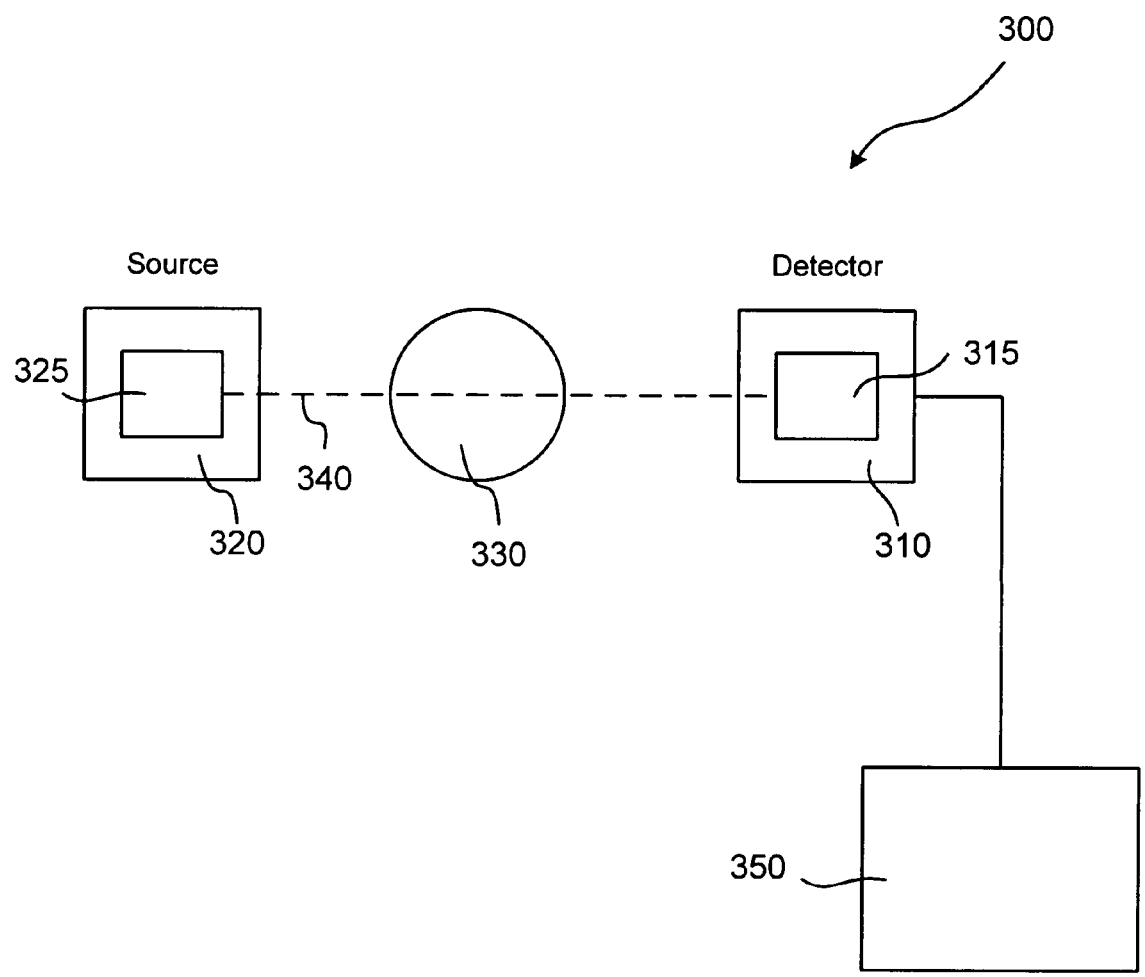
FIG. 3 shows a schematic view of an example embodiment of the present invention.

FIG. 3 illustrates one embodiment of a system 300 according to the present invention. A detector 310 includes an atomic species 315 capable of absorbing ionizing radiation and having an absorption edge at a particular wavelength. A source 320 includes an atomic species 325 chosen to have a characteristic emission peak at a wavelength that substantially matches the wavelength of the absorption edge of the detector species 315. Source 320 and detector 310 are positioned with respect to a volume 330 to deliver an ionizing radiation 340 to volume 330. Detector 310 is positioned to detect ionizing radiation 340 that passes through and/or by volume 330. Detector 310 is in communication with a general computing device 350 for processing information from detector 310 and producing an image.

A characteristic emission peak wavelength substantially matches the wavelength of an absorption edge when the characteristic emission peak wavelength is at or below the wavelength of the absorption edge and within a band of wavelengths not so far down the absorption curve of the detector that the relative absorption coefficient drops below approximately 50% of that of the absorption edge. The relative absorption coefficient varies in proportion to the wavelength to the 3rd power and is a known calculation. Thus, to achieve a relative absorption coefficient that is above about 50% of the relative absorption of absorption edge, a characteristic emission peak should have a wavelength that is within about 20% of the wavelength of the absorption edge and corresponds to about a 50% drop in relative absorption from the absorption edge. To achieve a relative absorption coefficient that is above about 80% of the relative absorption of an absorption edge, a characteristic emission peak should have a wavelength that is within about 7% of the wavelength of the absorption edge and corresponds to about a 20% drop in relative absorption from the absorption edge. To achieve a relative absorption coefficient that is above about 90% of the relative absorption of an absorption edge, a characteristic emission peak should have a wavelength that is within about 1% of the wavelength of the absorption edge and corresponds to about a 10% drop in relative absorption from the absorption edge. For example, with a xenon (Xe) detector and a tungsten (W) source, the absorption edge is at 0.358 angstroms and the closest characteristic radiation peak is at 0.214 angstroms, placing the relative absorption coefficient at approximately 22%. This is below the desired relative absorption coefficient (50%) for substantial matching.

In one example, a characteristic emission peak wavelength of a source is substantially matched to an absorption edge of a detector species. The characteristic emission peak wavelength in this example is at a wavelength that is at or below the absorption edge and corresponds to a relative absorption of the detector species that is not less than about fifty percent below the relative absorption at the absorption edge. In another example, a characteristic emission peak wavelength of a source is substantially matched to an absorption edge of a detector species. The characteristic emission peak wavelength in this example is at a wavelength that is at or below the absorption edge and corresponds to a relative absorption of the detector species that is not less than about twenty percent below the relative absorption at the absorption edge. In yet another example, a characteristic emission peak wavelength of a source is substantially matched to an absorption edge of a detector species. The characteristic emission peak wavelength in this example is at a wavelength that is at or below the absorption edge and corresponds to a relative absorption of the detector species that is not less than about ten percent below the relative absorption at the absorption edge. In still another example, a characteristic emission peak wavelength of a source is substantially matched to an absorption edge of a detector species. The characteristic emission peak wavelength in this example is at a wavelength that is at or below the absorption edge and corresponds to a wavelength from about 0.04 angstroms below said absorption edge to said absorption edge. In still yet another example, a characteristic emission peak wavelength of a source is substantially matched to an absorption edge of a detector species. The characteristic emission peak wavelength in this example is at a wavelength that is at or below the absorption edge and corresponds to a wavelength from about 0.03 angstroms below said absorption edge to said absorption edge. In still yet another example, a characteristic emission peak wavelength of a source is substantially matched to an absorption edge of a detector species. The characteristic emission peak wavelength in this example is at a wavelength that is at or below the absorption edge and corresponds to a wavelength from about 0.01 angstroms below said absorption edge to said absorption edge.

A detector according to the present invention includes any detector having an atomic species having an absorption edge that can be determined. Those of ordinary skill will appreciate various ways to construct and configure imaging detectors. In one embodiment, a detector includes a transparent and/or translucent ceramic solid-state device having an atomic species according to the present invention. Atomic species for inclusion in a detector may be selected such that the maximum absorption is at a desired wavelength. In another aspect, detector atomic species may be selected to match a pre-selected source atomic species. Example detector atomic species include, but are not limited to, erbium (Er), dysprosium (Dy), gadolinium (Gd), europium (Eu), samarium (Sm), neodynium (Nd), and any combinations thereof. A detector may include a mixture of atomic species. In one example, a detector includes a mixture of dysprosium and gadolinium.

A source according to the present invention includes any source having an atomic species for producing an ionizing radiation capable of producing an image in an imaging system. Those of ordinary skill will appreciate a variety of ways to configure a source for imaging once the desired imaging wavelengths and/or narrow imaging band of wavelengths are determined according to the present invention to correspond with a desired detector. Example sources include, but are not limited to, a particle accelerator, an atomic collider, a vacuum tube, and a radioactive atomic species. One example of a source configuration includes a high-voltage, rotating-anode, vacuum tube that generates an ionizing energy, such as x-ray, by the deceleration of high energy electrons (for example, 120 kV). In such a configuration, very little of the available kinetic energy from the deceleration of the electrons is actually converted into the ionizing energy. The remaining kinetic energy is converted into heat.

Heat is a common difficulty with imaging sources and management of this heat is a design challenge. In conventional sources, the selection of a source atomic species is typically limited to those that will withstand the high heats of operation. One benefit of the present invention is that careful matching of the absorption maximum of a detector with an emission peak of a source allows the intensity of the radiation used to be lowered, while still achieving desirable image quality. Lowering the intensity of the emitted radiation, lowers the heat of the source and allows the use of a wider range of source atomic species that have lower melting temperatures. Examples of lower melting point source atomic species include, but are not limited to, hafnium (Hf), iridium (Ir), osmium (Os), and any combinations thereof.

In another embodiment of the present invention, the ionizing energy provided to an object to be imaged is limited to wavelengths at or near an absorption edge of a detector atomic species. In yet another embodiment of the present invention, the ionizing energy provided to an object to be imaged is limited to wavelengths at or below an absorption edge of a detector atomic species. In still yet another embodiment of the present invention, the ionizing energy provided to an object to be imaged is limited to a narrow imaging band determined for a detector atomic species. A narrow imaging band includes a wavelength at or below an absorption edge of a detector and includes only wavelengths necessary to achieve a predetermined desired quality of resultant image. In determining the wavelengths necessary to achieve a predetermined image quality, the overall dose of ionizing radiation to reach the volume being imaged is balanced against the resultant image quality to use as little band width as possible to achieve the desired image quality. The overall dose of ionizing radiation is a function of the intensity of the radiation and the width of the source band reaching the volume. If a characteristic emission peak of a source is substantially matched to the absorption edge of a detector, the intensity can be greatly decreased over conventional approaches. Further decreases in ionizing energy dose can also be achieved by limiting the ionizing radiation to this narrow imaging band to a degree where the desired image quality can still be achieved. In an example where the characteristic emission peak of a source does not substantially match the absorption edge of the detector, significant reduction in dose can still be achieved by limiting the exposure to a narrow imaging band. In one example, a narrow imaging band includes a wavelength corresponding to the absorption edge of a detector. In another example, a narrow imaging band includes only wavelengths from about 0.04 angstroms below the absorption edge to about 0.005 angstroms above the absorption edge. In still another example, a narrow imaging band includes only wavelengths from about 0.01 angstroms below the absorption edge to about 0.005 angstroms above the absorption edge.

In a further embodiment of the present invention, an emission peak of a chosen source atomic species is selected to correspond to a desired imaging wavelength. In one example, an atomic species of a source is selected to have a k-alpha-2 peak corresponding to a desired imaging wavelength. In another example, an atomic species of a source is selected to have a k-alpha-1 peak corresponding to a desired imaging wavelength. In such an example, since the narrow imaging band of desired imaging wavelengths corresponds to wavelengths of maximum absorption by the detector and maximum emission by the source, it is possible to decrease the intensity of the source energy and achieve similar image resolution as that achieved using broad spectrum source energy at a higher intensity.

A source may include, or be accompanied by, a filter to assist in limiting wavelengths to the desired imaging wavelengths. In another aspect, source power voltage may be adjusted to assist in limiting wavelengths to the desired imaging wavelengths. Any atomic species capable of emitting energy at the desired imaging wavelength may be selected for inclusion in a source. Example source atomic species include, but are not limited to, rhenium (Re), tungsten (W), tantalum (Ta), molybdenum (Mo), niobium (Nb), and any combinations thereof. In one example, a source includes a mixture of atomic species.

A detector may be tuned to operate in a limited band of wavelengths by proper selection of filters or electronic modifications to the detector. In one example, a detector may be tuned to detect only wavelengths in a narrow imaging band including the absorption edge.

In another embodiment, the wavelength of the emission maximum of a source is matched closely to a narrow imaging band of wavelengths without limiting the overall emission to the narrow imaging band. By lowering the intensity of the source and closely matching the emission maximum and the absorption edge, quality images can be obtained at far lower radiation levels than in conventional imaging techniques.

Examples of ionizing radiation suitable for use in the present invention include, but are not limited to, x-ray radiation, gamma radiation, various subatomic particles, and any combinations thereof. In one example, ionizing radiation includes any short-wavelength ionizing radiation capable of producing an image of a object. In another example, ionizing radiation includes x-ray radiation. In yet another example, ionizing radiation includes gamma radiation.

Minimization of ionizing radiation provided to an object being imaged to a narrow band at or near the absorption edge of a detector, while providing a strong enough signal response for imaging, has benefits in many imaging applications. One example of such an imaging application is CT imaging. Example objects that can be imaged according to the present invention include, but are not limited to, a human, another living creature, food, baggage, a machine part, and any combinations thereof. In one aspect, an application for the present invention is in medical imaging. In another aspect, an application for the present invention is in experimental imaging. Minimizing ionizing radiation dose to many types of objects is desirable, whether animate, inanimate, young, or old. As mentioned above, children and infants are particularly susceptible to exposure to ionizing radiation. Minimizing radiation exposure in pediatric CT is one example of an application for the system and method of the present invention.

In another embodiment of the present invention, an existing imaging system may be modified to include a source and a detector according to the present invention. In one example, a source and a detector of an existing system can be replaced with a source and a detector having substantially matching wavelengths of maximum absorption and peak emission. In another example, a source and a detector of an existing system can be replaced with a source and a detector employing radiation limited to a narrow imaging band. In yet another example, the active materials (atomic species) of an existing source and detector may be replaced with source and detector atomic species according to the present invention. In still another example, an existing detector absorption maximum may be determined, a corresponding source provided to the existing system, and the existing detector configured to image at the desired imaging wavelengths.

Table 1 illustrates various absorption and emission values for sample detector atomic species and source atomic species. By comparing the wavelength of maximum absorption (the absorption edge) of an example detector species with emission peaks of various example source atomic species, advantageous combinations can be determined that provide a substantial match in absorption and emission maximums. Table 1 includes a calculation of the variance from the absorption edge to the K-Alpha-1 peak of various example atomic species. Although Table 1 includes select example atomic species, the present invention is not limited to these examples.

TABLE 1

| Detector Atomic Species | Detector Absorption Edge angstroms | Source Atomic Species | Source K-Alpha-1 angstroms | Source K-Alpha-2 angstroms | Detector Edge minus Source K-Alpha-1 angstroms | Source Melting Temp deg C. |
|---|---|---|---|---|---|---|
| Er | 0.215 | Re | 0.207 | 0.202 | 0.008 | 3180 |
|  |  | W | 0.214 | 0.209 | 0.001 | 3422 |
|  |  | Ta | 0.220 | 0.215 | −0.005 | 3015 |
| Dy | 0.230 | Re | 0.207 | 0.202 | 0.023 | 3180 |
|  |  | W | 0.214 | 0.209 | 0.016 | 3422 |
|  |  | Ta | 0.220 | 0.215 | 0.010 | 3015 |
| Dy-Gd Average | 0.238 | Re | 0.207 | 0.202 | 0.031 | 3180 |
|  |  | W | 0.214 | 0.209 | 0.024 | 3422 |
|  |  | Ta | 0.220 | 0.215 | 0.018 | 3015 |
| Gd | 0.246 | Re | 0.207 | 0.202 | 0.039 | 3180 |
|  |  | W | 0.214 | 0.209 | 0.032 | 3422 |
|  |  | Ta | 0.220 | 0.215 | 0.026 | 3015 |

In one embodiment of the present invention, erbium may be used as a detector atomic species. The absorption edge of erbium is at about 0.215 angstroms. Emission of a source atomic species may be selected to substantially match and be lower than the absorption edge of a detector. In one example, other source radiation (such as "white radiation") can be limited to a narrow imaging band by selection of tube voltage and appropriate filters. For the three closely matched source atomic species of rhenium, tungsten, and tantalum, the atomic species rhenium substantially matches the absorption maximum of erbium (Absorption Edge for Er minus K-alpha-1 for Re equal to 0.008 angstroms).

In another embodiment of the present invention, dysprosium may be used as a detector atomic species. The absorption edge of dysprosium is at about 0.230 angstroms. All three of the example source atomic species substantially match the absorption maximum of dysprosium with tantalum being the closest with a variance of 0.010 angstroms.

In yet another embodiment of the present invention, a 50:50 wt/wt mixture of dysprosium and gadolinium may be used as a detector atomic species. The absorption edge of the mixture is at about 0.238 angstroms. All three of the example source atomic species substantially match the absorption maximum of the mixture with tantalum being the closest with a variance of 0.018 angstroms.

In still another embodiment of the present invention, gadolinium may be used as a detector atomic species. The absorption edge of gadolinium is at about 0.246 angstroms. All three of the example source atomic species listed in Table 1 substantially match the absorption maximum of gadolinium with tantalum being the closest with a variance of 0.026 angstroms.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A system for imaging a volume, the system comprising:
   a detector having a first atomic species with an absorption edge having a first wavelength;
   a source having a second atomic species, said second atomic species for emitting an ionizing energy, said second atomic species selected to substantially match a second wavelength of a characteristic emission peak of said second atomic species to said first wavelength; and
   a filter element positioned between said second atomic species and the volume, said filter element for limiting said ionizing energy for delivery to the volume to a narrow imaging band of wavelengths including said second wavelength and including a wavelength at or below said absorption edge.

2. A system according to claim 1, wherein said second atomic species is selected so that said second wavelength corresponds to a relative absorption of said first atomic species that is not less than about fifty percent below the relative absorption at the peak of said absorption edge.

3. A system according to claim 1, wherein said second atomic species is selected so that said second wavelength corresponds to a relative absorption of said first atomic species that is not less than about twenty percent below the relative absorption at the peak of said absorption edge.

4. A system according to claim 1, wherein said second atomic species is selected so that said second wavelength corresponds to a relative absorption of said first atomic species that is not less than about ten percent below the relative absorption at the peak of said absorption edge.

5. A system according to claim 1, wherein said second atomic species is selected so that said second wavelength corresponds to a wavelength from about 0.04 angstroms below said absorption edge to said absorption edge.

6. A system according to claim 1, wherein said narrow imaging band is limited to wavelengths from about 0.04 angstroms below said first wavelength to about 0.005 angstroms above said first wavelength.

7. A system according to claim 1, wherein said first atomic species includes a species selected from the group consisting of erbium, dysprosium, europium, samarium, neodymium, gadolinium, lanthanum, and any combinations thereof.

8. A system according to claim 1, wherein said first atomic species includes a mixture of atomic species.

9. A system according to claim 1, wherein said second atomic species includes a species selected from the group consisting of rhenium, tungsten, molybdenum, niobium, tantalum, hafnium, iridium, osmium, and any combinations thereof.

10. A system according to claim 1, wherein said second atomic species includes tantalum.

11. A system according to claim 1, wherein said characteristic emission peak is a peak having a maximum emission intensity.

12. A system according to claim 1, wherein said characteristic emission peak includes a K-alpha-2 or a K-alpha-1 peak.

13. A system according to claim 1, wherein said ionizing energy includes x-ray energy.

14. A computer tomography device comprising:
    a system according to claim 1; and
    an image processor in communication with said detector for producing an image from information received from said detector, said information being related to said ionizing radiation that passes through the volume.

15. A system according to claim 1, wherein said source is positioned on a first side of the volume to deliver said ionizing energy to the volume and said detector is positioned on a second side of the volume to detect said ionizing energy once passed through the volume.

16. A system according to claim 1, wherein said detector is configured to generate an information that can be used to produce an image of the volume.

17. A method of producing a system for imaging a volume, the method comprising:
    providing a detector atomic species;
    determining a first wavelength of an absorption edge of said detector atomic species;
    selecting a source atomic species to substantially match a second wavelength of a characteristic emission peak of said source atomic species to said first wavelength;
    including said source atomic species in a source element, said source element for delivering an ionizing radiation to the volume;
    including said detector atomic species in a detector element, said detector element
    configured to detect said ionizing radiation that passes through the volume; and
    limiting said ionizing radiation for deliver to the volume to a narrow imaging band of wavelengths including said second wavelength and including a wavelength at or below said absorption edge.

18. A method according to claim 17, wherein said second atomic species is selected so that said second wavelength corresponds to a relative absorption of said first atomic species that is not less than about fifty percent below the relative absorption at the peak of said absorption edge.

19. A method according to claim 17, wherein said second atomic species is selected so that said second wavelength corresponds to a relative absorption of said first atomic species that is not less than about twenty percent below the relative absorption at the peak of said absorption edge.

20. A method according to claim 17, further comprising tuning said detector element to detect only wavelengths in a narrow imaging band including said absorption edge.

21. A method according to claim 17, wherein said narrow imaging band includes only wavelengths necessary to achieve a predetermined desired quality of said image.

22. A method according to claim 17, wherein said narrow imaging band is limited to wavelengths from about 0.04 angstroms below said first wavelength to about 0.005 angstroms above said first wavelength.

23. A method according to claim 17, wherein said first atomic species includes a species selected from the group consisting of erbium, dysprosium, europium, samarium, neodymium, gadolinium, lanthanum, and any combinations thereof.

24. A method according to claim 17, wherein said second atomic species includes a species selected from the group consisting of rhenium, tungsten, molybdenum, niobium, tantalum, hafnium, iridium, osmium, and any combinations thereof.

25. A method according to claim 17, wherein said second atomic species includes tantalum.

26. A method according to claim 17, wherein said ionizing energy includes x-ray energy.

27. A method of imaging a volume, the method comprising:
    providing a detector having a first atomic species with an absorption edge;
    providing a source having a second atomic species, wherein said second atomic species is selected to substantially match a characteristic emission peak of said second atomic species to said absorption edge;
    delivering an ionizing radiation from said source to the volume;
    using said detector to detect said ionizing radiation that passes through the volume;
    producing an image based on said ionizing radiation detected by said detector; and
    limiting said ionizing radiation for delivery to the volume to a narrow imaging band of wavelengths including a wavelength corresponding to said characteristic emission peak and including a wavelength at or below said absorption edge.

28. A method according to claim 27, further comprising limiting the intensity of said ionizing radiation delivered to the volume to a minimum level necessary to achieve a predetermined desired quality of said image.

29. A method according to claim 27, wherein said second atomic species is selected such that said characteristic emission peak has a wavelength that corresponds to a relative absorption value of said first atomic species that is not less than about fifty percent below the relative absorption at the peak of said absorption edge.

30. A method according to claim 27, wherein said second atomic species is selected such that said characteristic emission peak has a wavelength that corresponds to a relative absorption value of said first atomic species that is not less than about twenty percent below the relative absorption at the peak of said absorption edge.

31. A method according to claim 27, further comprising tuning said detector element to detect only wavelengths in a narrow imaging band including said absorption edge.

32. A method according to claim 27, wherein said narrow imaging band includes only wavelengths necessary to achieve a predetermined desired quality of said image.

33. A method according to claim 27, wherein said narrow imaging band is limited to wavelengths from about 0.04 angstroms below a first wavelength corresponding to said absorption edge to about 0.005 angstroms above said first wavelength.

34. A method according to claim 27, wherein said first atomic species includes a species selected from the group consisting of erbium, dysprosium, europium, samarium, neodymium, gadolinium, lanthanum, and any combinations thereof.

35. A method according to claim 27, wherein said second atomic species includes a species selected from the group consisting of rhenium, tungsten, molybdenum, niobium, tantalum, hafnium, iridium, osmium, and any combinations thereof.

36. A method according to claim 27, wherein said second atomic species includes tantalum.

37. A method according to claim 27, wherein said ionizing energy includes x-ray energy.

38. An imaging system for obtaining an image of a volume, the system comprising:
    a source operatively configured to provide an ionizing energy, said source including a first atomic species for producing said ionizing energy; and
    a detector comprising a second atomic species capable of absorbing said ionizing energy, said second atomic species having an absorption edge, said first and second atomic species being selected to substantially match said absorption edge and a characteristic emission peak of said first atomic species;
    wherein said source provides said ionizing energy to the volume at wavelengths limited to a narrow imaging band, said harrow imaging band including a wavelength at said characteristic emission peak, a wavelength at or below said absorption edge, and including only wavelengths necessary to achieve a predetermined desired quality of said image.

39. A system according to claim 38, wherein said narrow imaging band is limited to wavelengths from about 0.04 angstroms below a first wavelength corresponding to said absorption edge to about 0.005 angstroms above said first wavelength.

40. A system according to claim 38, wherein said narrow imaging band includes a wavelength corresponding to said absorption edge.

* * * * *

UNITED STATES PATENT AND TRADEMARK OFFICE
CERTIFICATE OF CORRECTION

PATENT NO. : 7,203,271 B2 Page 1 of 1
APPLICATION NO. : 11/169130
DATED : April 10, 2007
INVENTOR(S) : Benz et al.

It is certified that error appears in the above-identified patent and that said Letters Patent is hereby corrected as shown below:

In claim 17, column 10, line 47, delete "deliver" and insert -- delivery -- therefor.

In claim 38, column 12, line 39, delete "harrow" and insert -- narrow -- therefor.

Signed and Sealed this

Thirty-first Day of July, 2007

JON W. DUDAS
*Director of the United States Patent and Trademark Office*